United States Patent [19]
Zapol

[11] Patent Number: 5,396,882
[45] Date of Patent: Mar. 14, 1995

[54] GENERATION OF NITRIC OXIDE FROM AIR FOR MEDICAL USES

[75] Inventor: Warren M. Zapol, Concord, Mass.

[73] Assignee: The General Hospital Corporation, Boston, Mass.

[21] Appl. No.: 850,383

[22] Filed: Mar. 11, 1992

[51] Int. Cl.$^6$ ............................................. A61M 11/00
[52] U.S. Cl. ........................ 128/200.14; 128/202.25; 128/203.12
[58] Field of Search ...................... 128/200.14, 202.25, 128/202.26, 205.12, 203.12

[56] References Cited

U.S. PATENT DOCUMENTS

| | | | |
|---|---|---|---|
| 3,785,377 | 1/1974 | Jorgensen | 128/205.12 |
| 4,010,897 | 3/1977 | Treharne et al. | 239/8 |
| 4,287,040 | 9/1981 | Alamaro | 204/179 |
| 4,297,123 | 10/1981 | Wyse et al. | 71/58 |
| 4,336,798 | 6/1982 | Beran | 128/200.14 |
| 4,877,589 | 10/1989 | O'Hare | 422/186.24 |
| 4,915,915 | 4/1990 | Treharne | 422/186.24 |

OTHER PUBLICATIONS

Desai, K. M. et al., "Involvement of Nitric Oxide in the Reflex Relaxation of the Stomach to Accommodate Food or Fluid", p. 477, in *Nature*, vol. 351, No. 6, 1991.
Pepke-Zaba, Joanna et al., "Inhaled Nitric Oxide as a Cause of Selective Pulmonary Vasodilation in Pulmonary Hypertension", p. 1173, in *The Lancet*, vol. 338, No. 9, 1991.
Zapol, M. D., Warren, M., "Inhaled Nitric Oxide: A Selective Pulmonary Vasodilator Improving the Matching of Ventilation with Perfusion", Massachusetts General Hospital, Boston, Mass.
Roberts, Jr. et al. (Zapol), "Inhaled Nitric Oxide (NO): A Selective Pulmonary Vasodilator for the Treatment of Persistent Pulmonary Hypertension of the Newborn (PPHN)", p. 1279, in *Circulation*, vol. 84, No. 4, 1991.
Blomqvist et al. (Zapol), "Inhaled Nitric Oxide (NO): A Selective Pulmonary Vasodilator Reversing Human Hypoxic Pulmonary Vasoconstriction (HPV)", p. 361, in *Circulation*, vol. 84, No. 4, 1991.
Rimar et al., "Prolonged Duration of Inhaled Nitric Oxide Induced Vasodilation in Perfused Rabbit Lungs", p. 362, in *Circulation*, vol. 84, No. 4, 1991.
Donohoe et al., "Production of $O_3$, NO, and $N_2O$ in a Pulsed Discharge at 1 Atm", pp. 208–215, in *Ind. Eng. Chem.*, vol. 16, No. 2, 1977.
Fratacci et al., "Inhaled Nitric Oxide—A Selective Pulmonary Vasodilator of Heparin-Protamine Vasoconstriction in Sheep", pp. 990–999, in *Anesthesiology*, vol. 75, No. 6, 1991.
Frostell et al., "Inhaled Nitric Oxide—A Selective Pulmonary Vasodilator Reversing Hypoxic Pulmonary Vasoconstriction", pp. 2038–2047, in *Circulation*, vol. 83, No. 6, 1991.
Kolata, *The New York Times*, Jul. 2, 1991, p. C1.
Moncada et al., "Nitric Oxide: Physiology, Pathophysiology, and Pharmacology", pp. 109–142, in *Pharmacological Reviews*, vol. 30, 1990.
Ignarro et al., "Biosynthesis and Metabolism of Endothelium-derived Nitric Oxide", pp. 535–560, in *Annu. Rev. Pharmacol. Toxicol.*, vol. 30, 1990.

Primary Examiner—Edgar S. Burr
Assistant Examiner—Aaron J. Lewis
Attorney, Agent, or Firm—Fish & Richardson

[57] ABSTRACT

A system for producing a mixture comprising nitric oxide and air for treatment of medical conditions. The invention enables unlimited production of nitric oxide at any location using only air and a source of electricity. An electric arc chamber 4 is provided with electrodes 5 separated by an air gap 9. An electric circuit 7 supplies a high voltage potential to the electrodes 5 and induces an electric arc discharge across the electrodes 5. The electric arc discharge produces nitric oxide mixed with air. The mixture of nitric oxide and air is further purified and blended with other gases and/or pulmonary therapeutic agents, and the therapeutically-effective gas mixture is delivered to different organs of a human body using organ specific attachments.

25 Claims, 7 Drawing Sheets

Line voltage powered NO generator

Line voltage powered NO generator

GENERATION OF NITRIC OXIDE FROM AIR FOR MEDICAL USES

STATEMENT AS TO FEDERALLY SPONSORED RESEARCH

This invention was made in the course of work supported by the U.S. government which has certain rights in the invention.

BACKGROUND OF THE INVENTION

This invention relates to a method and a system for producing nitric oxide mixed with air or other gases for use in medicine.

Nitric oxide (NO) is crucial to many biological systems (G. Kolada, The New York Times, Jul. 2, 1991, p. C1.). Kolada indicates that nitric oxide mediates the control of blood pressure, helps the immune system kill invading parasites that enter cells, stops cancer cells from dividing, transmits signals between brain cells, and contributes to the large scale death of brain cells that can debilitate people with strokes or Huntington's disease.

It was shown that nitric oxide mediates relaxation of gastric smooth muscle (K. M. Desai et al., Nature, Vol. 351, Jun. 6, 1991, p. 477). Desai et al. demonstrated that adaptive relaxation in isolated stomach of the guinea pig is mediated by a non-adrenergic, non-cholinergic (NANC) neurotransmitter. Furthermore, they showed that this NANC neurotransmitter is undistinguishable from nitric oxide derived from L-arginine. The authors concluded that it is likely that nitric oxide is a final common mediator of smooth muscle relaxation.

Smooth muscle is present, for example, in the walls of the blood vessels, bronchi, gastrointestinal tract, and urogenital tract. Administration of nitric oxide gas to the lung by inhalation could produce localized smooth muscle relaxation without systemic side effects. This characteristic can be used in medicine to treat bronchial constriction and pulmonary hypertension, pneumonia, etc.

Nitric oxide is now known to be an important naturally occurring local cellular hormone, the so-called endothelium derived relaxing factor. This factor is produced in many cells (i.e., endothelial cells lining blood vessels, bronchi, intestines, bladder, uterus, and other hollow organs) by the enzyme nitric oxide synthetase (now known to be a family of at least six enzymes) from arginine. Once NO is released, it binds rapidly to the enzyme guanylate cyclase in smooth muscle cells, increasing cyclic guanylate monophosphate (cyclic GMP), reducing intracellular calcium levels and thereby causing smooth muscle relaxation.

Inhaled nitric oxide, as demonstrated by a number of pilot studies in animals and humans, is a potent local pulmonary vasodilator and bronchodilator with no systemic effects. NO has the remarkable ability to improve the matching of ventilation with perfusion, thereby increasing the injured lungs oxygen transport efficiency and raising the arterial oxygen tension. To date, NO is the only pulmonary vasoactive agent known with such selective properties and thus has enormous potential in the treatment of acute and chronic lung diseases with pulmonary bronchoconstriction and vasoconstriction.

Bronchodilators are drugs which are used to reduce airway reactivity and to reverse bronchospasm caused by a variety of diseases, such as asthma, exacerbations of chronic pulmonary obstructive disease, allergic and anaphylactic reactions and others. Several classes of bronchodilators have been employed, each with its own mode of action, tolerance and undesirable side effects.

Beta agonists, represented by epinephrine and isoproterenol, induce bronchodilation by stimulating receptors that increase adenyl cyclase concentrations and the production of intracellular cyclic adenosine monophosphate (AMP). They can be delivered by aerosol, orally or parenterally. Administration of these agents causes significant adverse cardiac effects such as tachycardias, heart palpitations, changes in blood pressure and also other side effects including anxiety, tremors, nausea and headaches. Newer, beta$_2$-selective agonists, for example, albuterol have fewer side effects and somewhat slower onset of action.

Theophylline preparations are less potent bronchodilators than beta agonists and have a narrower therapeutic toxic window. The mechanism responsible for the bronchodilator effect of theophylline is probably via cyclic AMP. Side effects commonly caused by theophylline are nervousness, nausea, vomiting, anorexia and headache. Furthermore, if taken at very high levels, theophylline can cause cardiac arrhythmias and seizures.

Anticholinergic drug such as atropine methylnitrate and ipratrobium bromide administered by aerosol are effective bronchodilators with relatively few side effects. However, they have a slow onset of action, and 60 to 90 minutes may be required before peak bronchodilation is achieved.

Nitric oxide is unique in that it combines a rapid onset of action occurring within seconds with the absence of systemic effects. Once inhaled, it diffuses through the pulmonary vasculature into the bloodstream, where it is rapidly inactivated by combination with hemoglobin. Therefore, the bronchodilator effects of inhaled nitric oxide are limited to the airway and the vasodilatory effects of inhaled nitric oxide are limited to the pulmonary vasculature.

This unique ability of nitric oxide to dilate pulmonary vessels selectively can be used also in the treatment of either acute or chronic pulmonary hypertension. Pulmonary hypertension is defined as an elevation of the mean pulmonary arterial pressure over the normal levels of 12 to 15 millimeters Hg.

Acute pulmonary hypertension is produced by vasoconstriction of pulmonary vessels in response to sudden hypoxia due to, for example, pneumonia, pulmonary embolus, or acidosis. Acute pulmonary hypertension is a potentially reversible phenomenon and successful treatment of the precipitating condition leads to normalization of the pulmonary pressures. Persistent hypoxia, however, induces permanent structural changes in the pulmonary vasculature, and chronic pulmonary hypertension ensues. The main causes of chronic pulmonary hypertension are chronic obstructive pulmonary disease, recurring multiple small emboli, heart disease such as mitral stenosis or atrial septal defect, and idiopathic primary pulmonary hypertension. Pulmonary hypertension has also been implicated in several other life-threatening conditions such as adult respiratory distress syndrome and persistent pulmonary hypertension of the newborn.

To date, treatment of pulmonary hypertension has been attempted with several vasodilator drugs including nitroprusside, hydralazine, nifedipine, captopril and others. Major limitation of these agents has been their non-selective reduction of both pulmonary and systemic blood pressures. In contrast, inhaled nitric oxide produces vasodilation limited to pulmonary vessels and thus offers a revolutionary therapeutic advantage.

An inhaler designed to deliver nitric oxide is described in U.S. patent application Ser. No. 07/767,234, filed Sep. 23, 1991, assigned to the same assignee as this application, and incorporated herein by reference.

SUMMARY OF THE INVENTION

The present invention is a system for producing a mixture of nitric oxide and air or other gases for use in medicine. The system generates nitric oxide in an electric arc discharge using only air and a source of electricity. The invention enables unlimited production of nitric oxide at any location.

A patient can carry a portable inhaler version of the invented system anywhere he or she goes and use the inhaler for treatment of asthma attacks or other forms of bronchoconstriction, of acute respiratory failure, or reversible pulmonary vasoconstriction. Furthermore, the patient can vary the inhaled amount of NO as his or her medical condition changes.

The invention system can be used in medical or urgent care facilities for generating NO and delivering a therapeutically-effective concentration of NO mixed with other gases to a specific organ of a human body. Nitric oxide relaxes smooth muscles almost immediately after delivery; moreover, the action of nitric oxide is limited only to the organ subjected to the treatment.

In one aspect, the invention is an inhaler producing a mixture of air or other gases and nitric oxide for respiratory therapy; the inhaler utilizes a source of electricity to generate an electric arc across a pair of electrodes separated by an air gap. Air is continuously introduced through an air input port to an electric arc chamber which contains the electrodes. The inhaler has an electric circuit for supplying a high voltage potential to the electrodes, wherein the high voltage potential has a peak value sufficient to induce the electric arc across the air gap. The arc discharge produces nitric oxide. The produced nitric oxide mixed with air is dispensed through an output port and is inhaled by a patient.

Preferred embodiments of this aspect of the invention may include electrodes made of two axially aligned metal rods with their tips separated by an adjustable air gap placed in the arc chamber. The circuitry of the inhaler comprises a high voltage transformer with the primary coil connected to an electric power supply, and a parallel RCL circuit connected in parallel to the secondary, high voltage coil of the transformer. The resistive element of the parallel RCL circuit comprises the high voltage electrodes separated by the air gap. The air input port of the inhaler has a filter for filtering introduced air through the input port to prevent liquid droplets or solid particles from entering the arc chamber. The inhaler is of a hand-held size and weighs less than approximately 1 kg.

Preferred embodiments of this aspect of the invention may also include a purifying device for removing the low levels of nitrogen dioxide and ozone produced in the arc chamber. The purifying device is located so that gas leaving the arc chamber is forced through the purifying device before it is released from the inhaler. The output port also has a mouthpiece for directly inhaling the gas mixture from the arc chamber forced through the purifying device.

Preferred embodiments of this aspect of the invention may also include an air input assembly with a set of selective restricting orifices for introducing a controlled amount of air to the inhaling port and blending the air with the gas mixture from the arc chamber while inhaling the mixture though the mouthpiece. The purifying device contains a scavenger for $O_3$ and $NO_2$, such as sodalime or baralime.

Preferred embodiments of this aspect of the invention may also include a gas pump for forcing the gas mixture through the purifying device out the output port. The gas mixture then enters an oxygen mask or is forced into a room or chamber, such as an incubator.

In another aspect, the invention is a system for continuously producing a mixture of air and nitric oxide for treatment of medical conditions requiring direct delivery of this mixture to an organ of the human body. The system has an electric arc chamber with a pair of electrodes separated by an air gap, for producing nitric oxide by arc discharge between the electrodes. The system also has an electric circuit for supplying a high voltage potential to the electrodes. The high voltage potential has a peak value sufficient to induce an electric arc across the air gap. An air input port of the system is used for continuously introducing air into the electric arc chamber. A gas delivery system is used for purifying and dispensing the produced nitric oxide mixed with air or other gases to an organ of the human body, for example, administering the mixture (to which other gases, e.g., anesthesia could be added) to the lung using a mechanical ventilator or respirator.

Preferred embodiments of this aspect of the invention may also include a gas input manifold for introducing selected gases into the delivery system, for precisely blending the selected gases with the produced nitric oxide air mixture, and for dispensing the blend by the delivery system.

Preferred embodiments of this aspect of the invention may also include a gas analyzer (e.g. $NO_x$ chemiluminescence analyzer) for analyzing the concentration of individual constituents of said blend of gases dispensed by the delivery system. A regulator system connected to the analyzer and the gas input manifold is used for controlling the concentration of individual gaseous constituents (e.g., inspired oxygen concentration) introduced into the delivery system according to a predetermined prescription scheme.

Other features and advantages of the invention will be apparent from the following description of the preferred embodiments, and from the claims.

DESCRIPTION OF THE PREFERRED EMBODIMENTS

Figure 1:
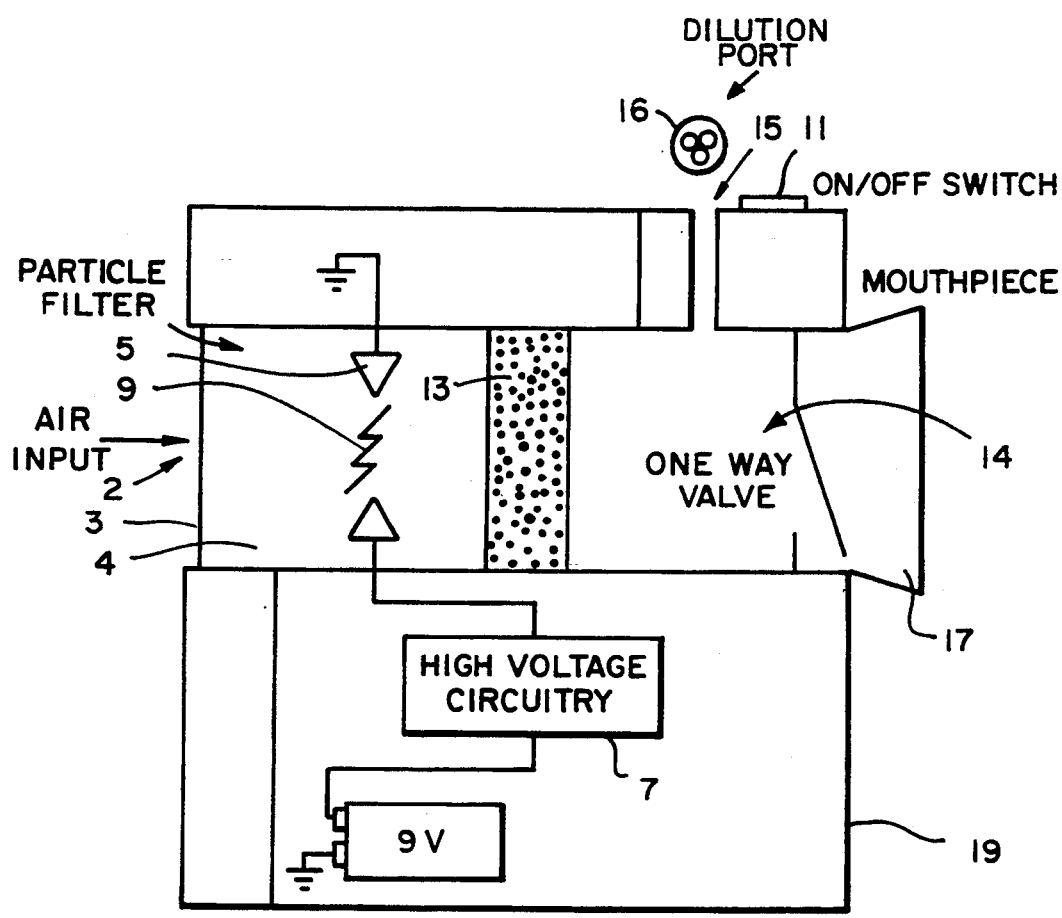
FIG. 1 is a diagrammatic cross-sectional view of a portable inhaler embodiment of the invention.

Shown in FIG. 1 is a portable inhaler with an input port 2 for introducing air into an electric arc chamber 4. Input port 2 contains a one way valve and a 0.22 micron filter 3 made by Millipore Corp. The filter removes bacteria and undesirable constituents present in the introduced air. Arc chamber 4, made of an electrically insulating material, has two axially positioned electrodes 5 separated by an air gap 9. A high voltage generating circuit 7 is connected to the electrodes 5. Electric arc chamber 4 is coupled to a sodalime filter 13 which is attached to an inhaling port 14. Inhaling port 14 has a mouthpiece 17 and an air input assembly 15 comprised of a set of selectable restricting orifices 16. Each orifice has a filter for filtering liquid droplets and solid particles present in the air. The gas passage system (including input port 2, filters 3, 13, and inhaling port 14) is designed to allow easy, relatively unrestricted inhalation by the patient. Different types of filters can be employed according to the environmental conditions in which the inhaler is used. The inhaler is enclosed in a case 19 made of Teflon® or another high voltage insulator. A power switch 11 with a pilot light controls operation of the inhaler.

Figure 2:
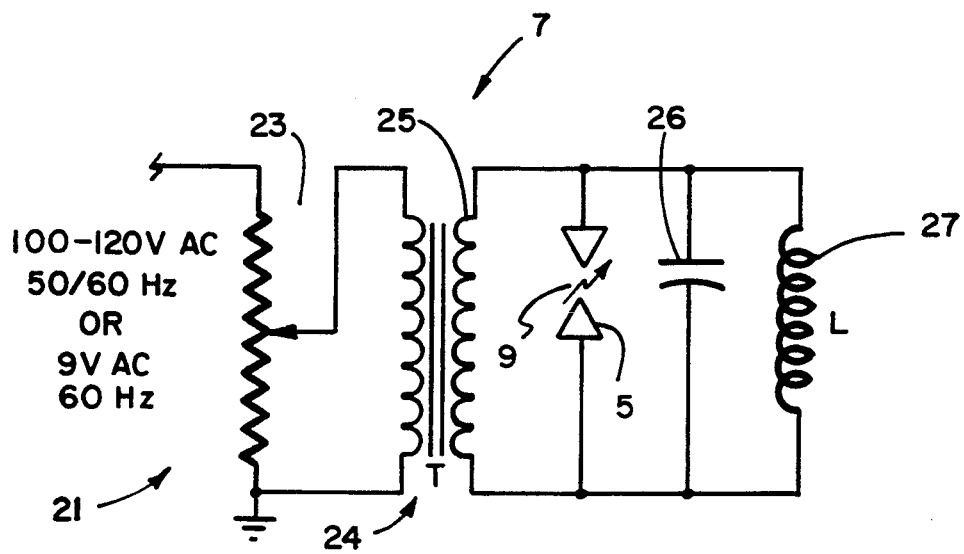
FIG. 2 shows a schematic diagram of a high voltage generating circuit for embodiments.

Referring to FIG. 2, a high voltage generating circuit 7 consists of a step up transformer 24 with primary and secondary coils. The primary coil is connected to a power supply 21, and secondary, high voltage coil 25 is connected to a parallel RCL circuit. Voltage from power supply 21 is regulated by a variac 23 and transformed to higher values in a secondary coil 25. Other circuits for generating high energy voltages, such as a Tesla coil, could also be used. The electric energy is temporarily stored in a capacitor 26 which is charged up to breakdown voltage and subsequently discharged across air gap 9. Air gap 9 defined by two electrodes 5 determines the resistance of the two electrode arrangement. The breakdown voltage ($\approx 20$ kV) is proportional to the width of the air gap and the shape of electrodes 5.

The electric arc discharge produces plasma localized across the air gap. In plasma, molecules of oxygen and nitrogen are broken and the atoms ionized to form ozone and nitric oxide. A small fraction of nitric oxide then oxidizes to a higher oxidation state and forms nitrogen dioxide ($NO_2$). However, this process is significant only at elevated temperatures. The concentrations of NO, $NO_2$ and $O_3$ vary depending upon the width of the air gap and the duration of the electric arc, and are expressed as parts per million by volume (ppm).

In the operation of the inhaler, the gases are drawn out from arc chamber 4, through sodalime filter 13, and out of inhaling port 14 by a patient inhaling the gas mixture through mouthpiece 17. Sodalime filter 13 removes toxic $NO_2$ and $O_3$ from the gas mixture preventing them from reaching the inhaling port, so that it contains primarily air and NO. At the same time additional air enters the inhaler through input port 2 and is drawn into arc chamber 4. Subsequent arc discharges ionize the $N_2$ and $O_2$ molecules which form NO, $NO_2$, and $O_3$, and the process is repeated. The concentration of NO produced in the arc discharge chamber varies from 10 to 250 ppm depending on the resistance of air gap 9 and the power delivered to electrodes 5. The therapeutically beneficial range of NO concentration (for a portable inhaler) is from about 1 ppm to 180 ppm. In order to achieve these values of NO concentration in the inhaled gas, an additional air admixing input port 15 with the set of restricting orifices 16 of different sizes is used as an air intake port. A patient breathing in the gases from the inhaler through the mouthpiece 17 automatically mixes the gases from the arc chamber with air entering input port 15. To vary NO concentration the patient can select a different size of the orifice in order to increase or decrease the amount of air drawn into inhaling port 14 through air input port 15. In another embodiment, wherein a patient is unable to inhale, a gas pump, or other pressure source (e.g., ventilator), is incorporated into inhaling port 14 to force the gas mixture out of the inhaler. The mouthpiece could then be attached to an endotracheal tube or tracheostomy tube. This electrical NO generator can be attached to a standard gas powered multidose inhaler (MDi), which ejects a chemical bronchodilator (e.g., terbutaline, corticosteroid, etc.) into port 15. Following several seconds inhaling electrically produced NO to produce immediate bronchodilation, the MDi is activated to produce longer duration bronchodilation. This will increase the efficiency of the MDi by improving the delivery of drug to the NO dilated bronchi. It is also possible to inject other inhaled drugs with electrocally produced NO (either NO before or with NO) such as surfactants, mucolytics, etc.

In the preferred embodiment, the inhaler is a portable lightweight hand-held battery powered unit of less than approximately $20 \times 20 \times 10$ cm in size. A patient suffering from asthma or pulmonary hypertension can carry the inhaler, and use it according to his or her needs. Initially, the patient might need to inhale larger doses of nitric oxide, for example, in a concentration of 150 ppm of nitric oxide in air; this can be done by closing air input port 15. As the patient's bronchi and/or pulmonary vessels dilate, he or she can decrease this concentration by choosing a larger orifice. The hand-held inhaler provides an unlimited supply of NO.

Figure 3:
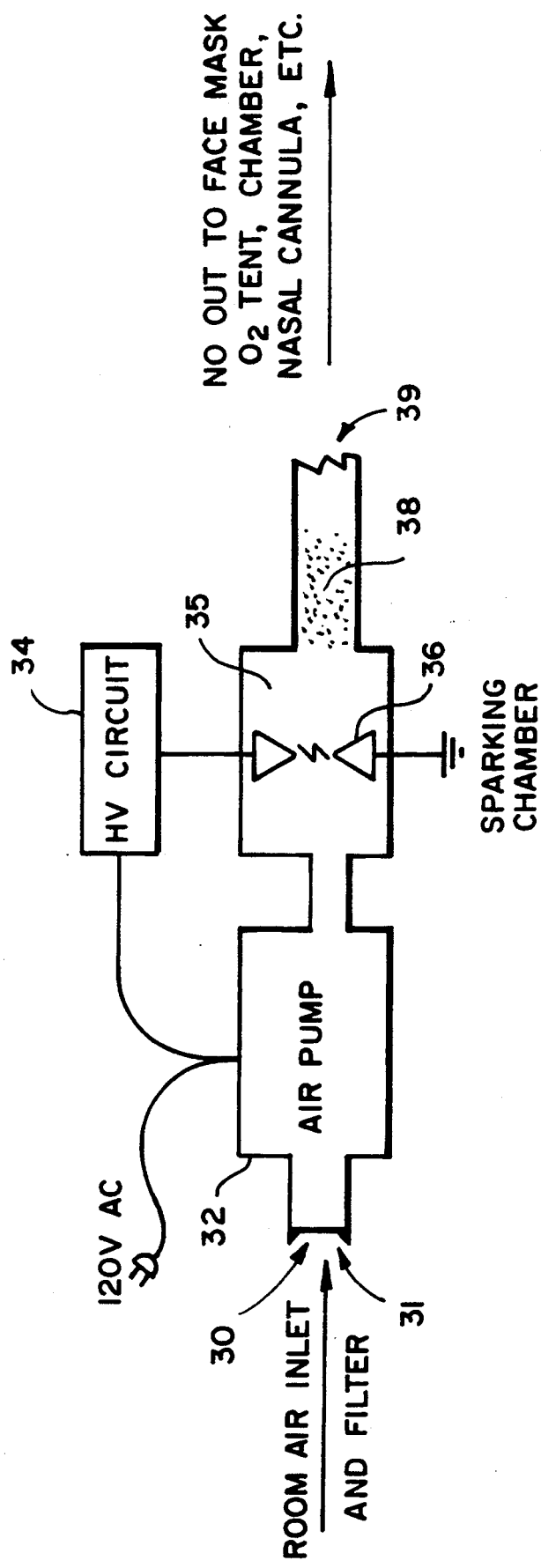
FIG. 3 is a diagrammatic cross-sectional view of a larger inhaler embodiment for use at home.

In another preferred embodiment, the inhaler is a larger system for use at home. Referring to FIG. 3, an air pump 32 forces air to an electric arc chamber 35. A filter 31 located at an input port 30 removes undesirable constituents present in the introduced air. Similarly as in the portable inhaler embodiment, the arc chamber made of an electrically insulating material has two electrodes 36 separated by an air gap. Electrodes 36 are connected to a high voltage circuit 34 powered by a standard 110 V, 60 Hz (or 220 V, 50 Hz) outlet. Nitric oxide, nitrogen dioxide, and ozone produced in the arc discharge are forced through a sodalime filter 38. Filter 38 absorbs $NO_2$ and $O_3$ from the gas mixture. Nitric oxide mixed with air or other gases (e.g. $O_2$) is pumped out of an output port 39 which can be connected to a face mask. In another preferred embodiment, the produced gas mixture is pumped into an incubator or a room through output port 39.

Figure 4:
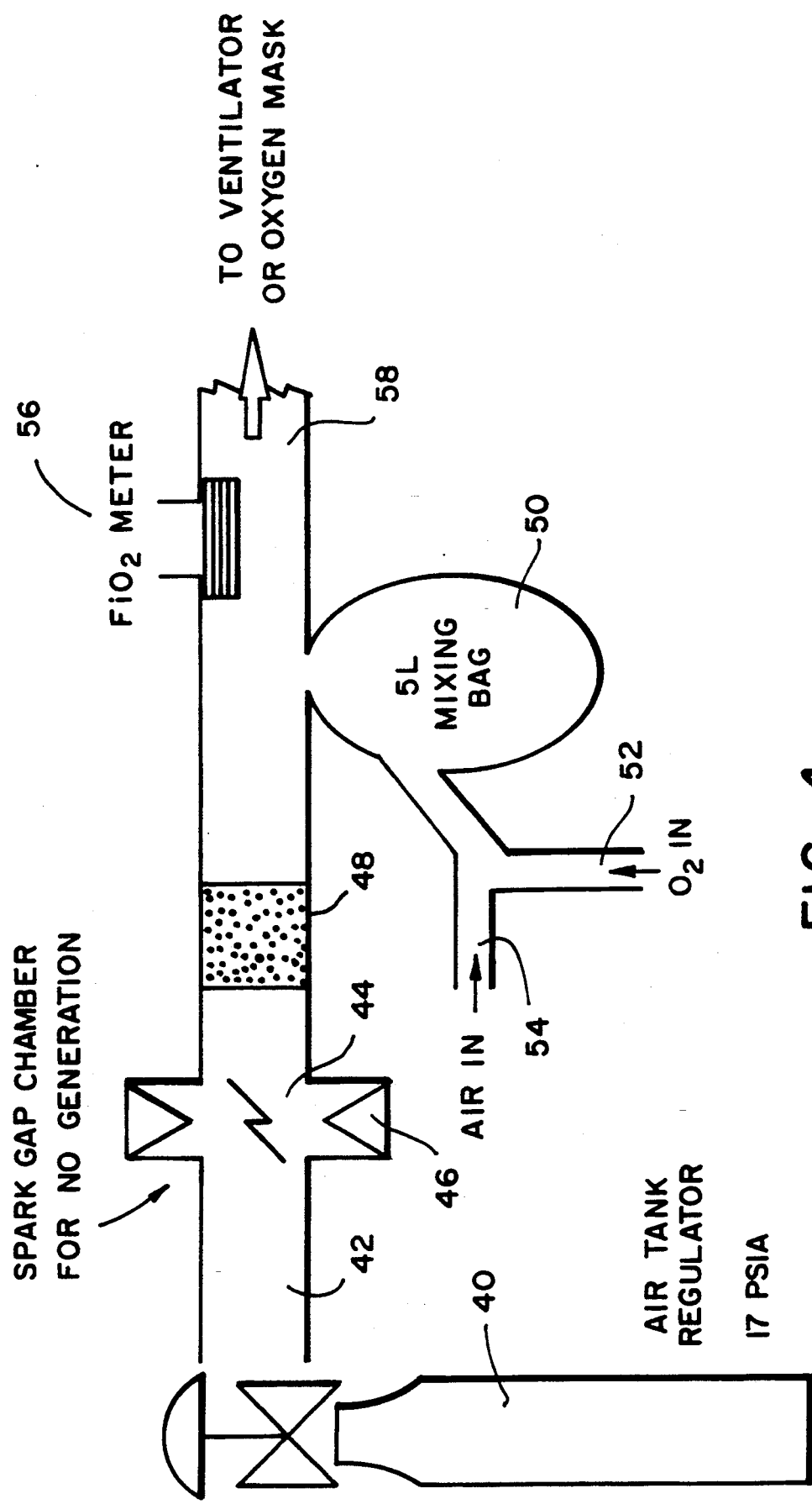
FIG. 4 is a diagrammatic cross-sectional view of an inhaler system embodiment for use in medical and urgent care facilities.

In another preferred embodiment, the inhaler is a unit used in medical and urgent care facilities. Size of the inhaler depends on the particular use. A large unit is powered by a standard 110 V, 60 Hz power outlet, and a portable unit by a 9 V battery. Referring to FIG. 4, an air tank and regulator 40 is utilized to supply air pressurized at 17 psi to the NO generation system. Similarly as in the other embodiments, the system has an input port 42, an arc chamber 44 with electrodes 46, and a sodalime filter 48. The mixture of NO and air is generated in the same way as discussed earlier. In addition, this system has a five liter mixing bag 50 connected to an output port 58. Mixing bag 50 is used to blend air supplied through a port 59 and oxygen or oxygen rich $N_2$ mixture supplied through a port 52. The mixture of air, oxygen, and NO is introduced through the output port 58 to a ventilator or to an oxygen mask. An inspired oxygen fraction (FiO$_2$) meter 56 is attached to output port 58 to measure the proportion of $O_2$ gas, by volume.

Figure 5:
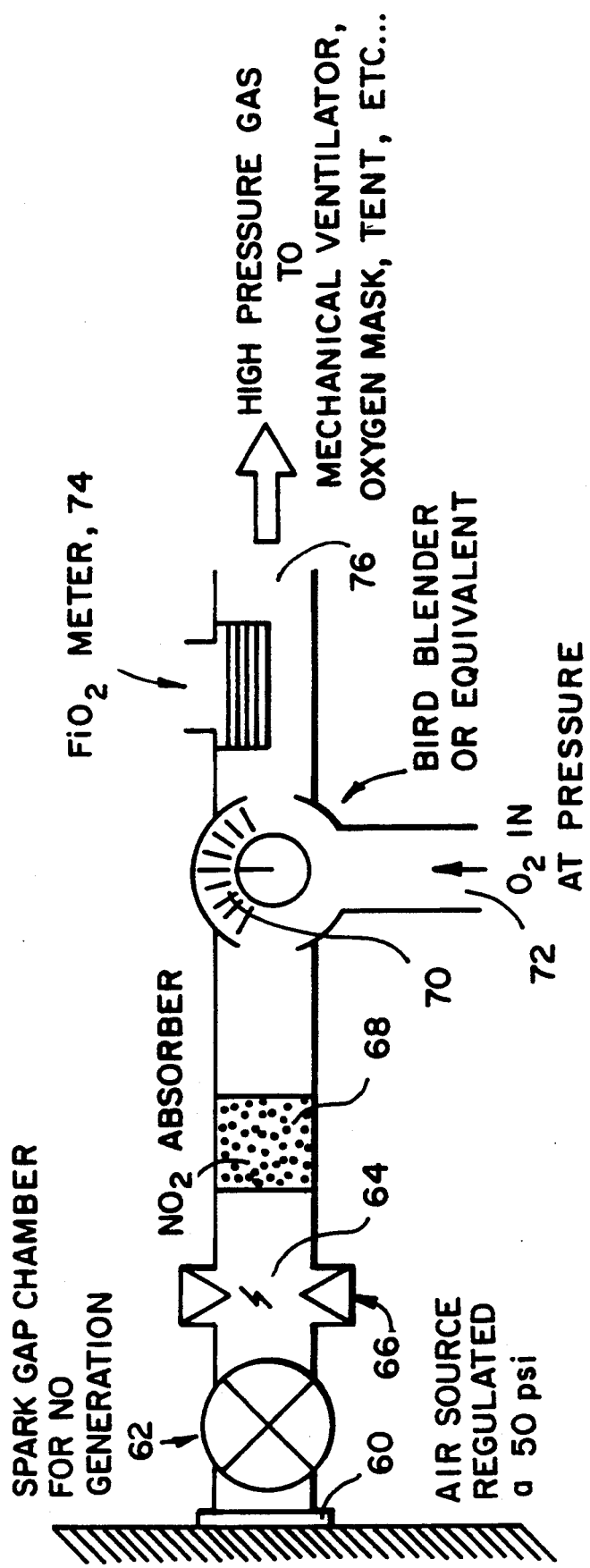
FIG. 5 is a diagrammatic cross-sectional view of another embodiment, for delivering nitric oxide to different organs of a human body, including a mechanical ventilator for respiratory support.

In another preferred embodiment, the invention is a system used in medical facilities such as an intensive care unit or emergency room. Referring to FIG. 5, a source 60 of air pressurized near 50 psi is used in this system. The arc chamber of this larger unit could contain more than one pair of electrodes in order to increase the amount of produced nitric oxide. The arrangement of this unit is similar to the one shown in FIGS. 1, 3 and 4. The pressurized air is introduced through a regulator 62 to an arc chamber 64 where electrodes 66 are located. A sodalime filter 68 absorbs the unwanted by-products of the arc discharge process (i.e. $NO_2$ and $O_3$). The mixture of air and NO is blended by a Bird blender 70 with oxygen supplied through a port 72. An FiO$_2$ meter 74 attached to an output port 76 measures the $O_2$ proportion. The system is powered by a standard 110 V, 60 Hz power source. In addition, the unit can have an automatic regulator system and a gas analyzer connected to the air intake port and to the gas pump. The gas analyzer monitors the amounts of nitric oxide and other gases in the mixture of gases delivered to an organ of a human body; in addition, the analyzer manages the automatic regulator system in order to maintain a specific concentration of nitric oxide according to a predetermined scheme. This embodiment could be attached to a mechanical ventilator and used to provide NO gas mixtures for ventilatory therapy.

Different attachments (not shown in FIG. 5) could be secured to output port 76 to deliver mixtures of various gases and nitric oxide to specific organs. For example, output port 76 can be fitted with an attachment which delivers NO to the tip of a Foley catheter to enable an easy insertion of the catheter into the urinary bladder. As is apparent from the foregoing, the mixtures of NO and air produced by the apparatus of FIGS. 1–5 are not stored for later use but are immediately delivered to the patient. As discussed in U.S. patent application Ser. No. 07/767,234 (incorporated by reference), such immediate use reduces conversion of NO to $NO_2$.

EXAMPLE 1

Figure 6:
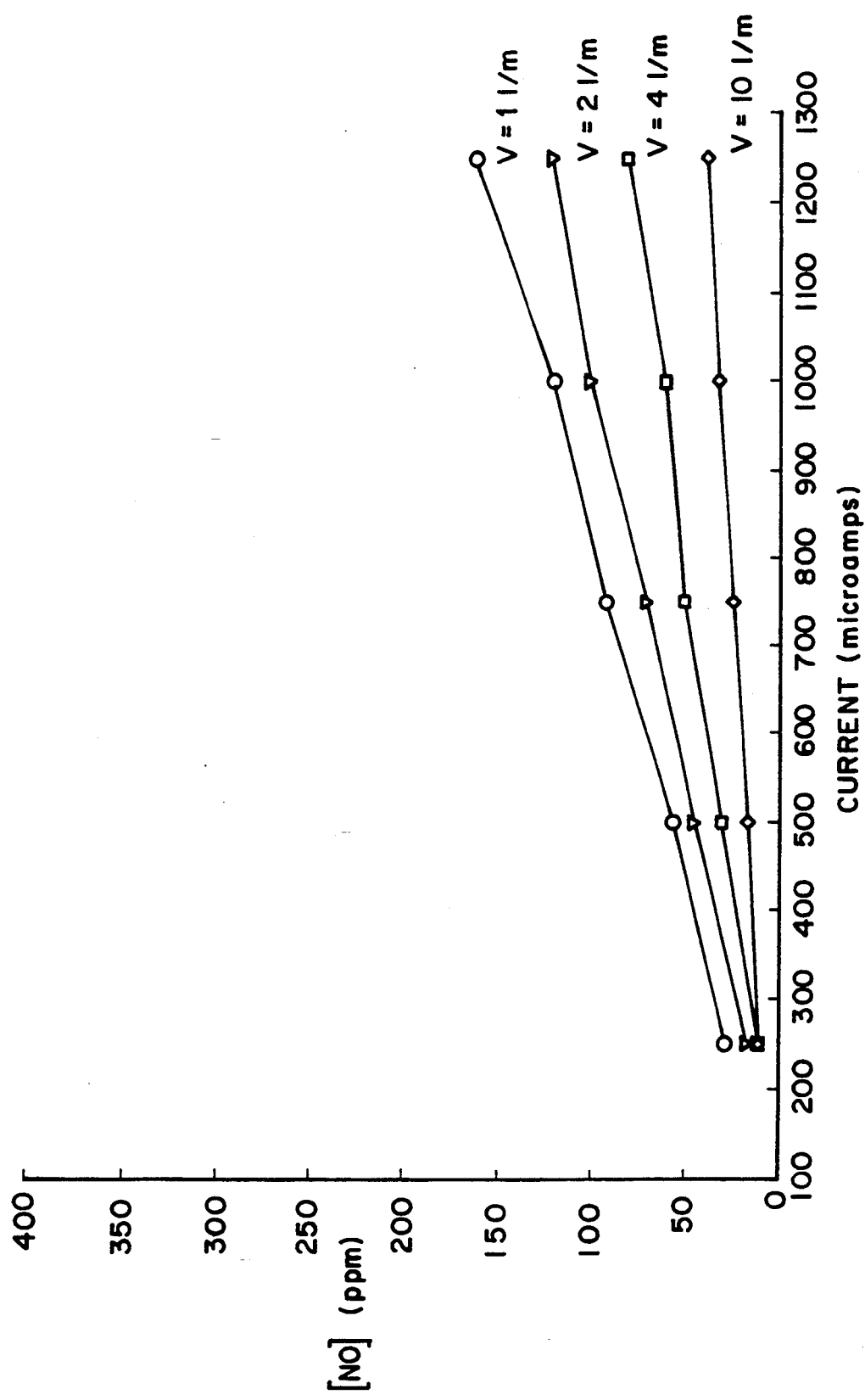
FIG. 6 is a graph depicting the dependence of effluent gas nitric oxide concentration on the average current in the primary coil of the high voltage transformer and the flow rate of air through the arc chamber, for a 3 mm gap between the electrodes, where V is air flow rate in liters/minute, and the NO level is in parts per million volume (ppm).
Figure 7:
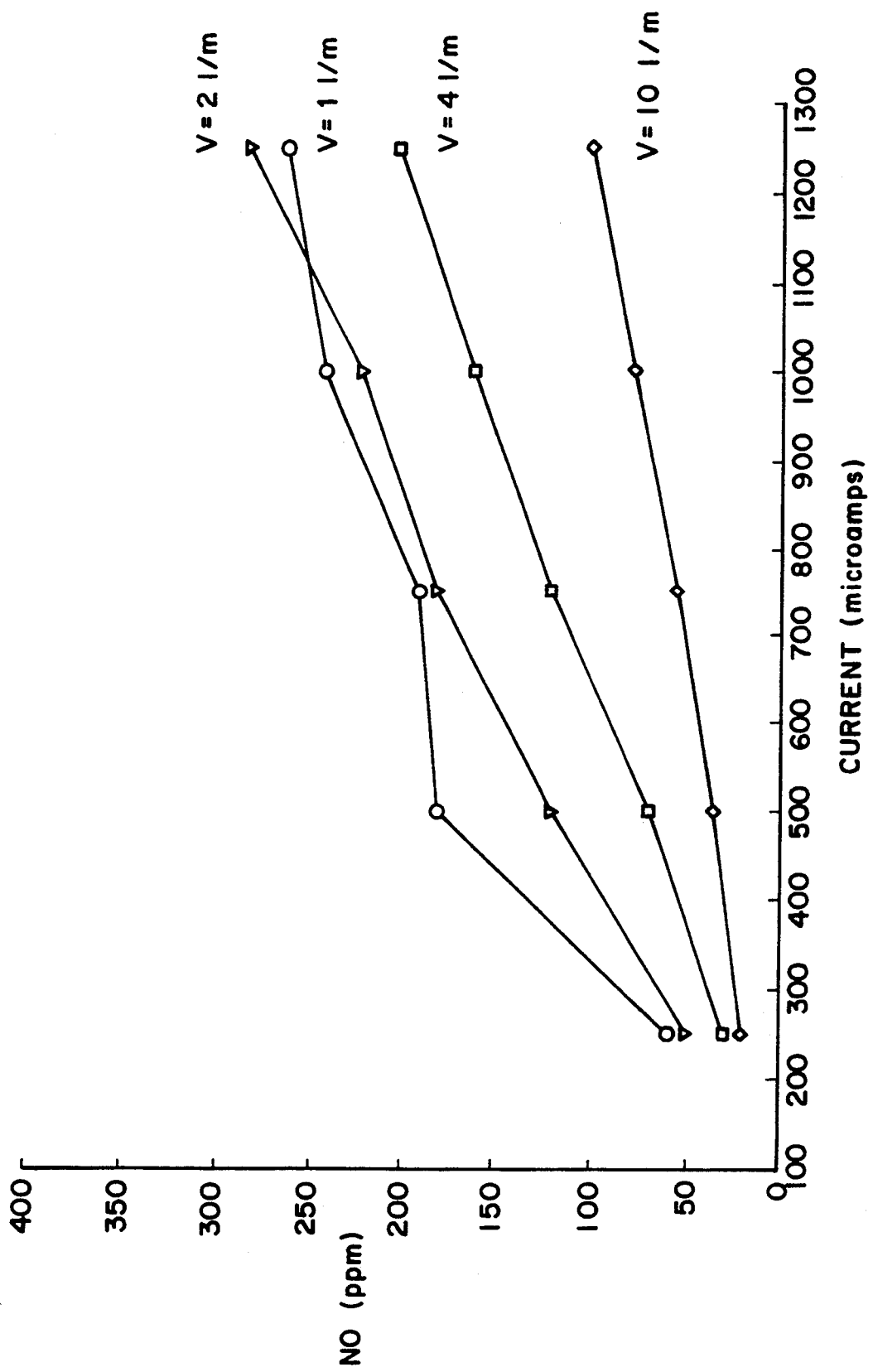
FIG. 7 is a graph depicting the dependence of effluent gas nitric oxide concentration on the current in the primary coil of the high voltage transformer and the flow of air through the arc chamber, for a 5 mm gap between the electrodes, where V is air flow in liters/minute, and the NO level is in parts per million volume (ppm).

Performance of a test unit is shown in FIGS. 6 and 7 for 3 mm and 5 mm gaps between the electrodes, respectively. Different flow levels (V) of air in the range from 1 liter/minute (l/m) to 10 l/m are introduced into the arc chamber. Current in the primary coil of the high voltage transformer is varied from 250 $\mu$A to 1.25 mA in order to increase the power supplied to the high voltage generating circuit. The output from the arc chamber is drawn into a $NO_x$ chemiluminescence gas analyzer in order to establish the concentrations of the different oxides of nitrogen.

Referring to FIG. 6, the concentration of NO, expressed in parts per million, increases monotonically with power supplied to the electrodes, which have 3 mm separation. The highest concentration of nitric oxide is obtained for an air flow (V) of 1 l/m; further increase in the flow rate of air decreases NO concentration.

Nearly the same trend is observed for the gap of 5 mm, shown in FIG. 7. However, due to the larger air gap, the plasma created in the arc discharge is larger, and thus, the arc discharge produces a higher concentration of NO. The voltage necessary to break the dielectric and to create a spark across the electrodes is about 20 kV. Separating the electrodes further would require a larger breakdown voltage.

The ozone level produced in the electric arc discharge was measured by an ultraviolet photometric ozone analyzer. The NO generation system with a spark gap of 3 mm at a 2 l/m air flow rate produced 0.01 ppm of ozone in the arc discharge chamber. This $O_3$ level is substantially below the ozone exposure limit established by the U.S. Department of Labor, the Occupational Safety and Health Administration. The $NO_2$ levels were similarly measured at very low levels (<2% of NO levels).

The optimal operating regime is around 1.1 mA with the air flow of about 1.5 l/m. However, these parameters are dependent on the shape of the electrodes, humidity of air and other factors.

EXAMPLE 2

Figure 8:
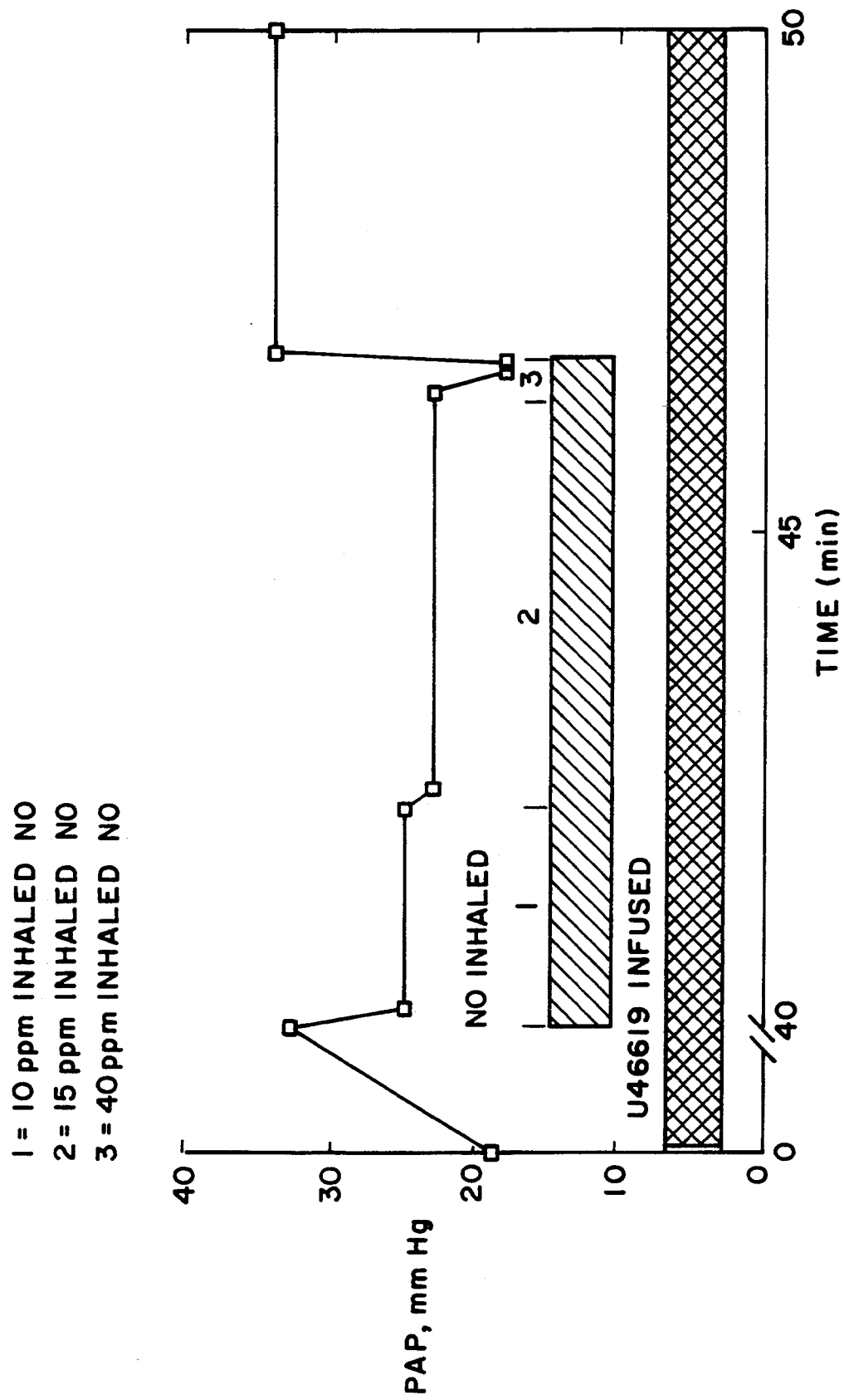
FIG. 8 is a graph depicting the dependence of the pulmonary arterial pressure during different stages of an NO inhalation trial on an awake sheep with acute pulmonary hypertension due to infusion of U46619. The NO gas was produced by electric discharge, and shows marked pulmonary vasodilatory properties.

A 30 kg male Dorset sheep with a tracheostomy was instrumented with a 7 Fr pulmonary artery Swan-Ganz catheter and femoral arterial line for constantly monitoring pulmonary and systemic arterial pressures. The awake sheep was given a continuous infusion of 0.6 $\mu$g/kg/min of U46619 (Upjohn Pharmaceuticals), a stable thromboxane analog capable of producing acute pulmonary vasoconstriction and hypertension. The infusion of U46619 caused the pulmonary arterial pressure (PAP) to increase 79% from the mean baseline value of 19 mm Hg to 33 mm Hg. An electric arc and circuit similar to FIG. 4 was used to generate a mixture of air and NO. Immediately upon inhaling 10 ppm NO in air, the PAP decreased 25% to 25 mm Hg, confirming the vasodilating action of NO generated electrically by a high voltage DC spark across a 5 mm air gap. FIG. 8 shows the dependence of the mean PAP on different levels of inhaled NO measured continuously by chemiluminescence. When increasing the spark current to obtain 15 ppm inhaled NO concentration, the PAP decreased to a level of 23 mm Hg. Additional increase of the inhaled NO to 40 ppm further reduced the PAP to its baseline level without U46619 infusion of 18 mm Hg. Subsequently, only air was delivered to the sheep's lung causing a rapid increase in the PAP to 34 mm Hg due to the unopposed action of the infused U46619. The systemic arterial pressure (SAP) remained constant at 94 mm Hg throughout the course of this NO inhalation trial. The fact that SAP remained constant provides evidence that inhaled NO acts only as a local vasodilator of the pulmonary circulation.

Other embodiments of the invention are within the scope of the claims. In referring to "air" in the claims, it is also intended to include ordinary air as well as other mixtures of gas comprising $N_2$ and $O_2$. Various other gases, e.g., anesthetics, additional $O_2$, other bronchodilating drugs (e.g., multidose inhalers), or other drugs for pulmonary therapy (e.g., surfactants, mucolytics, anti-inflammatory agents), etc. may be added to the mixture of nitric oxide and air produced by the embodiments of the invention.

What is claimed is:

1. An inhaler producing a mixture comprising air and nitric oxide for respiratory therapy, said inhaler utilizing air and a source of electricity, said inhaler comprising an electric arc chamber with a pair of electrodes separated by an air gap, for producing nitric oxide by an arc discharge between said electrodes, an electric circuit for supplying a high voltage potential to said electrodes, said high voltage potential having a peak value sufficient to induce an electric arc across said air gap, a gas input port for introducing air into said electric arc chamber, thereby producing a mixture of air and NO, and an output port for dispensing said produced mixture for inhaling by a patient, said output port and said electric arc chamber being sized and positioned so that said produced mixture is immediately dispensed from said output port.

2. The inhaler of claim 1 wherein said electrodes of said arc chamber are two axially aligned metal rods with their tips separated by said air gap.

3. The inhaler of claim 1 or 2 further comprising
   a purifying device for removing nitrogen dioxide and ozone produced in said arc chamber, said purifying device being located so that said gas mixture leaving said arc chamber is forced through said purifying device, and
   a gas pump for forcing said gas mixture out said output port.

4. The inhaler of claim 2 wherein said circuitry comprises
   a high voltage transformer having the primary side connected to an electric power supply,
   a parallel RCL circuit connected in parallel to the secondary, high voltage side of said high voltage transformer wherein the resistive element of said parallel RCL circuit comprises said high voltage electrodes separated by said air gap.

5. The inhaler of claim 1, 2 or 4 wherein said air input port includes a filter for filtering said introduced air through said input port to prevent liquid droplets or solid particles from entering said arc chamber.

6. The inhaler of claim 5 wherein said inhaler is less than approximately 20×20×10 cm in size and a weight less than approximately 1 kg.

7. The inhaler of claim 5 further comprising
   a purifying device for removing nitrogen dioxide and ozone produced in said arc chamber, said purifying device being located so that gas leaving said arc chamber is being forced through said purifying device before being released from said inhaler, and
   a mouthpiece at said output port for directly inhaling said gas mixture from said arc chamber through said purifying device.

8. The inhaler of claim 7 wherein said purifying device contains a scavenger for $O_3$ and $NO_2$.

9. The inhaler of claim 7 further comprising an air input assembly having a set of selective restricting orifices for introducing controlled amount of air to said inhaling port and blending said air with said gas mixture from said arc chamber while inhaling said mixture though said mouthpiece.

10. A system for continuously producing a mixture, comprising air and nitric oxide for treatment of medical conditions requiring direct delivery of said mixture to an organ of the human body, said system comprising an electric arc chamber with a pair of electrodes separated by an air gap, for producing nitric oxide by arc discharge between said electrodes, an electric circuit for supplying a high voltage potential to said electrodes, said high voltage potential having a peak value sufficient to induce an electric arc across said air gap, an gas input port for introducing air or ventilatory gases into said electric arc chamber, thereby producing a mixture of air and NO, and a delivery system for dispensing said produced mixture to an organ of the human body, said delivery system and said electric arc chamber being sized and positioned so that said produced mixture is immediately dispensed from said output port.

11. The system of claim 10 wherein said delivery system is configured to dispense said mixture directly to a specific organ.

12. The system of claim 11 further comprising a gas input manifold for introducing selected gases into said delivery system, blending said selected gases with said mixture and dispensing said blend by said delivery system.

13. The system of claim 12 further comprising
    a gas analyzer for analyzing the concentration of individual constituents of said blend of gases being dispensed by said delivery system, and
    a regulator system connected to said analyzer and said gas input manifold for controlling the concentration of individual constituents being introduced into said delivery system according to a predetermined prescription scheme.

14. The device of claim 1 or 10 further comprising means for adding additional gases to said mixture.

15. A method of producing a mixture comprising air and nitric oxide for respiratory therapy, said method utilizing air and a source of electricity, comprising the steps of:

introducing air through an air input port into an electric arc chamber of an inhaler, supplying high voltage potential to a set of electrodes separated by an air gap and located in said electric arc chamber, said high voltage potential having a peak value sufficient to induce an electric arc across said air gap, producing a mixture of air and nitric oxide by an arc discharge between said electrodes charged to said high voltage potential, and immediately dispensing said produced mixture through an output port for immediate use for respiratory therapy.

16. The method of claim 15 further comprising the step of purifying gas drawn from said arc chamber in order to remove nitrogen dioxide and ozone produced during said arc discharge.

17. The method of claim 15 further comprising the step of blending said mixture of nitric oxide and air drawn in from said arc chamber with air introduced through an air input assembly having a set of selective restricting orifices.

18. The method of claim 15 further comprising the step of purifying gas drawn in from said arc chamber in order to remove nitrogen dioxide and ozone produced during said arc discharge.

19. The method of claim 15 further comprising the step of forcing said gas mixture out of said output port using a gas pump.

20. The method of claim 15 further comprising the step of filtering said introduced air through said input port in order to prevent liquid droplets or solid particles from entering said arc chamber.

21. The method of claim 15 further comprising the step of adding additional gases to said mixture.

22. A method of producing nitric oxide for treatment of medical conditions by utilizing direct organ specific delivery of said gas mixture, comprising the steps of:

introducing air through an air input port into an electric arc chamber of said system, supplying high voltage potential to a set of electrodes separated by an air gap and located in said electric arc chamber, said high voltage potential having a peak value sufficient to induce an electric arc across said air gap, producing a mixture of air and nitric oxide by an arc discharge between said electrodes charged to said high voltage potential, and immediately dispensing said produced nitric oxide mixed with air through a delivery system designed for immediately dispensing said gas mixture to a specific organ of a patient's body.

23. The method of claim 22 wherein said nitric oxide is delivered to a specific organ.

24. The method of claim 22 further comprising the step of introducing selected gases through a gas input manifold into said delivery system, blending said selected gases with said produced mixture of nitric oxide and air, and dispensing said blend by said delivery system.

25. The method of claim 24 further comprising the steps of:

analyzing concentration of individual constituents of said blend of gases being dispensed by said delivery system, and regulating concentration of individual constituents being introduced into said delivery system using a regulating system connected to a gas analyzer and said gas input manifold according to a predetermined prescription scheme.

* * * * *